United States Patent
Wang et al.

(10) Patent No.: US 7,352,370 B2
(45) Date of Patent: Apr. 1, 2008

(54) FOUR-DIMENSIONAL VOLUME OF INTEREST

(75) Inventors: Hongwu Wang, Milpitas, CA (US); John R. Dooley, Castro Valley, CA (US); Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 229 days.

(21) Appl. No.: 11/144,247

(22) Filed: Jun. 2, 2005

(65) Prior Publication Data

US 2006/0274061 A1 Dec. 7, 2006

(51) Int. Cl.
*G06T 17/00* (2006.01)
*G06K 9/00* (2006.01)
(52) U.S. Cl. .................. 345/424; 382/131; 382/154
(58) Field of Classification Search ............... 600/3, 600/411, 424, 427; 382/131, 154; 345/424
See application file for complete search history.

(56) References Cited

U.S. PATENT DOCUMENTS

| | | | | |
|---|---|---|---|---|
| 4,706,296 A * | 11/1987 | Pedotti et al. ............... 382/278 |
| 4,788,975 A * | 12/1988 | Shturman et al. ............. 606/7 |
| 5,359,513 A * | 10/1994 | Kano et al. ................. 382/128 |
| 5,384,861 A * | 1/1995 | Mattson et al. ............. 382/131 |
| 5,396,418 A * | 3/1995 | Heuscher ..................... 378/15 |
| 5,633,951 A * | 5/1997 | Moshfeghi ................... 382/154 |
| 5,798,982 A * | 8/1998 | He et al. ..................... 367/73 |
| 5,802,220 A | 9/1998 | Black et al. |
| 6,139,500 A * | 10/2000 | Clark ......................... 600/443 |
| 6,169,817 B1 | 1/2001 | Parker et al. |
| 6,307,914 B1 | 10/2001 | Kunieda et al. |
| 6,438,403 B1 * | 8/2002 | Cline et al. ................. 600/410 |
| 6,466,813 B1 * | 10/2002 | Shukla et al. ............... 600/411 |
| 6,473,634 B1 * | 10/2002 | Barni ......................... 600/425 |
| 6,539,074 B1 * | 3/2003 | Yavuz et al. ................. 378/4 |
| 6,563,941 B1 * | 5/2003 | O'Donnell et al. .......... 382/131 |
| 6,728,424 B1 | 4/2004 | Zhu et al. |
| 6,757,423 B1 * | 6/2004 | Amini ........................ 382/154 |
| 6,835,137 B1 * | 12/2004 | Nakamura ................... 463/42 |
| 6,892,089 B1 * | 5/2005 | Prince et al. ............... 600/410 |
| 6,995,763 B2 * | 2/2006 | Gatti et al. ................. 345/424 |
| 7,031,504 B1 * | 4/2006 | Argiro et al. ............... 382/131 |
| 7,107,089 B2 * | 9/2006 | Lee ........................... 600/424 |
| 7,154,498 B2 * | 12/2006 | Cowan et al. .............. 345/419 |
| 7,218,320 B2 * | 5/2007 | Gordon et al. ............. 345/419 |
| 7,256,787 B2 * | 8/2007 | Hung et al. ................. 345/473 |
| 7,280,686 B2 * | 10/2007 | Hornegger et al. ......... 382/154 |

(Continued)

OTHER PUBLICATIONS

Leksell, L., "The stereotactic method and radiosurgery of the brain", Acta Chirurgica Scandanavica 102 (1951), pp. 316-319.

(Continued)

*Primary Examiner*—Mark Zimmerman
*Assistant Examiner*—Crystal Murdoch
(74) *Attorney, Agent, or Firm*—Blakely, Sokoloff, Taylor & Zafman LLP

(57) ABSTRACT

A method and apparatus for representing a deformable volume of interest in four dimensions is described, where the four dimensions are three spatial dimensions and one temporal dimension including discrete points in time, and where the deformable volume of interest can be represented at intermediate points in time by interpolation.

28 Claims, 9 Drawing Sheets

U.S. PATENT DOCUMENTS

| | | | |
|---|---|---|---|
| 7,286,866 B2* | 10/2007 | Okerlund et al. | 600/407 |
| 7,295,692 B2* | 11/2007 | Nay et al. | 382/131 |
| 2001/0048731 A1* | 12/2001 | Nakamura et al. | 378/4 |
| 2002/0054699 A1* | 5/2002 | Roesch et al. | 382/131 |
| 2002/0172407 A1* | 11/2002 | O'Donnell et al. | 382/131 |
| 2002/0177770 A1* | 11/2002 | Lang et al. | 600/410 |
| 2003/0072479 A1* | 4/2003 | Totterman et al. | 382/131 |
| 2003/0142868 A1* | 7/2003 | Tannenbaum et al. | 382/199 |
| 2003/0184291 A1* | 10/2003 | Rehwald et al. | 324/307 |
| 2003/0228905 A1* | 12/2003 | Osako | 463/32 |
| 2004/0081270 A1* | 4/2004 | Heuscher | 378/4 |
| 2004/0138548 A1* | 7/2004 | Strommer et al. | 600/407 |
| 2004/0158145 A1* | 8/2004 | Ghelmansarai et al. | 600/427 |
| 2004/0258289 A1* | 12/2004 | Hornegger | 382/130 |
| 2005/0027187 A1* | 2/2005 | Barth et al. | 600/407 |
| 2005/0053267 A1* | 3/2005 | Mostafavi | 382/128 |
| 2005/0074145 A1* | 4/2005 | Liu et al. | 382/109 |
| 2005/0083332 A1* | 4/2005 | Hung et al. | 345/473 |
| 2005/0111720 A1* | 5/2005 | Gurcan et al. | 382/131 |
| 2005/0182316 A1* | 8/2005 | Burdette et al. | 600/424 |
| 2005/0261570 A1* | 11/2005 | Mate et al. | 600/411 |
| 2006/0002601 A1* | 1/2006 | Fu et al. | 382/132 |
| 2006/0002630 A1* | 1/2006 | Fu et al. | 382/294 |
| 2006/0020195 A1* | 1/2006 | Falco et al. | 600/407 |
| 2006/0072799 A1* | 4/2006 | McLain | 382/128 |
| 2006/0074292 A1 | 4/2006 | Thomson et al. | |
| 2006/0078183 A1* | 4/2006 | deCharms | 382/128 |
| 2006/0149522 A1* | 7/2006 | Tang | 703/11 |
| 2006/0182326 A1* | 8/2006 | Schildkraut et al. | 382/132 |
| 2007/0133848 A1* | 6/2007 | McNutt et al. | 382/128 |

OTHER PUBLICATIONS

Holder, A., "A tutorial on radiation oncology and optimization", In Greenberg, H.J., ed.: Tutorials on Emerging Methodologies and Applications in Operations Research. Kluwer Academic Press (2004).

Ferris, M., Lim, J., Shepard, D.: "An optimization approach for the radiosurgery treatment planning", SIAM Journal on Optimization 13 (2003), pp. 921-937.

Cheek, S., Holder, A., Fuss, M. Salter, B.: "The relationship between the number of shots and the quality of Gamma Knife Radiosurgeries." Technical Report 84, Department of Mathematics, Trinity University, San Antonio, TX (2004).

Rosen, I., Lane, R., Morrill, S., Belli, J.: "Treatment plan optimization using linear programming", Medical Physics 18 (1991), pp. 141-152.

Shepard, D., Ferris, M., Olivera, G., Mackie, T.: "Optimizing the delivery of radiation therapy to cancer patients", SIAM Review 41 (1999) pp. 721-744.

Bartolozzi, F., De Gaetano, A., DiLena, E., Marino, S., Nieddu, L., Patrizi, G.: "Operational research techniques in medical treatment and diagnosis: a review." European Journal of Operations Research 121 (2000) pp. 435-466.

Holder, A.: "Radiotherapy treatment design and linear programming". Technical Report 70, Department of Mathematics, Trinity University, San Antonio, TX (2002).

Dantzig, G.B., Orden, A., Wolfe, P.: "The generalized Simplex method for minimizing a linear form under linear inequality restraints". Pacific Journal of Mathematics 5 (1955), pp. 183-195.

Paddick, I.: "A simple scoring ratio to index the conformality of radiosurgical treatment plans", Journal of Neurosurgery 93 (2000), pp. 219-222.

D. Bechmann, N. Dubreuil, "Animation through space and time base don a space deformation model", The Journal of Visualization and Computer Animation, 4(3) 165-184, 1993.

M. Levoy, et al., "Volume Rendering in Radiation Treatment Planning", Proc. First Conference on Visualization in Biomedical Computing, IEEE Computer Society Press, Atlanta, Georgia, May 1990, pp. 4-10.

Jay B. West, Calvin R. Maurer, Jr., John R. Dooley, Hybrid point-and-intensity-based deformable registration for abdominal CT images, Medical Imaging 2005: Image Processing, edited by J. Michael Fitzpatrick, Joseph M. Reinhardt, Proc. of SPIE vol. 5747, pp. 204-211.

Torsten Rohlfing et al., "Modeling liver motion and deformation during the respiratory cycle using intensity-based nonrigid registration of gated MR images", Med. Phys. 31 (3), Mar. 2004, pp. 427-432.

* cited by examiner

FOUR-DIMENSIONAL VOLUME OF INTEREST

TECHNICAL FIELD

This invention relates to the field of radiation treatment planning and, in particular, to a volume of interest applied to treatment planning.

BACKGROUND

A non-invasive method for pathological anatomy (e.g., tumor, legion, vascular malformation, nerve disorder, etc.) treatment is external beam radiation therapy. In one type of external beam radiation therapy, an external radiation source is used to direct a sequence of x-ray beams at a pathological anatomy site from multiple angles, with the patient positioned so the pathological anatomy is at the center of rotation (isocenter) of the beam. As the angle of the radiation source is changed, every beam passes through the pathological anatomy site, but passes through a different area of healthy tissue on its way to the pathological anatomy. As a result, the cumulative radiation dose at the pathological anatomy is high and the average radiation dose to healthy tissue is low. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centi-Gray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Traditionally, medical imaging was used to represent two-dimensional views of the human anatomy. Modern anatomical imaging modalities such as computed tomography (CT) are able to provide an accurate three-dimensional model of a volume of interest (e.g., skull or pathological anatomy bearing portion of the body) generated from a collection of CT slices and, thereby, the volume requiring treatment can be visualized in three dimensions. More particularly, in CT scanning numerous x-ray beams are passed through a volume of interest in a body structure at different angles. Then, sensors measure the amount of radiation absorbed by different tissues. As a patient lies on a couch, an imaging system records x-ray beams from multiple points. A computer program is used to measure the differences in x-ray absorption to form cross-sectional images, or "slices" of the head and brain. These slices are called tomograms, hence the name "computed tomography."

During treatment planning, a volume of interest (VOI) from anatomical (e.g., CT) and/or functional imaging is used to delineate structures to be targeted or avoided with respect to the administered radiation dose. A volume of interest (VOI) may be defined as a set of planar, closed polygons, as illustrated in FIG. 1A. The coordinates of the polygon vertices are defined as the x/y/z offsets in a given unit from the image origin. Once a VOI has been defined, it may be represented as a bit wise mask overlaid on the functional and/or anatomical image (so that each bit is zero or one according to whether the corresponding image volume pixel (voxel) is contained within the VOI represented by that bit), or a set of contours defining the boundary of the VOI in each image slice. Conventional VOI imaging architectures may utilize a three-tier representation structure: VOI-contourslice-contour. FIG. 1B illustrates the three-tier VOI structure in a Unified Modeling Language (UML) graph with a sample VOI.

One problem encountered in external beam radiation treatment is that pathological anatomies (e.g., a tumor) may move during treatment, which decreases accurate target localization (i.e., accurate tracking of the position of the target). Most notably, soft tissue targets tend to move with patient breathing during radiation treatment delivery sessions. Respiratory motion can move a pathological anatomy in the chest or abdomen, for example, by more than 3 centimeters (cm). In the presence of such respiratory motion, for example, it is difficult to achieve the goal of precisely and accurately delivering the radiation dose to the target, while avoiding surrounding healthy tissue. In external beam radiation treatment, accurate delivery of the radiation beams to the pathological anatomy being treated can be critical, in order to achieve the radiation dose distribution that was computed during the treatment planning stage.

Conventional methods for tracking anatomical motion utilize external markers and/or internal fiducial markers. Such conventional methods do not enable modeling of the anatomical change due to the respiratory cycle using conventional VOI imaging architectures. Moreover, such conventional methods do not take into account non-rigid motions and deformations of surrounding anatomy, as a function of motion cycle.

BRIEF DESCRIPTION OF THE DRAWINGS

The present invention is illustrated by way of example, and not by way of limitation, in the figures of the accompanying drawings.

DETAILED DESCRIPTION

Figure 1A:
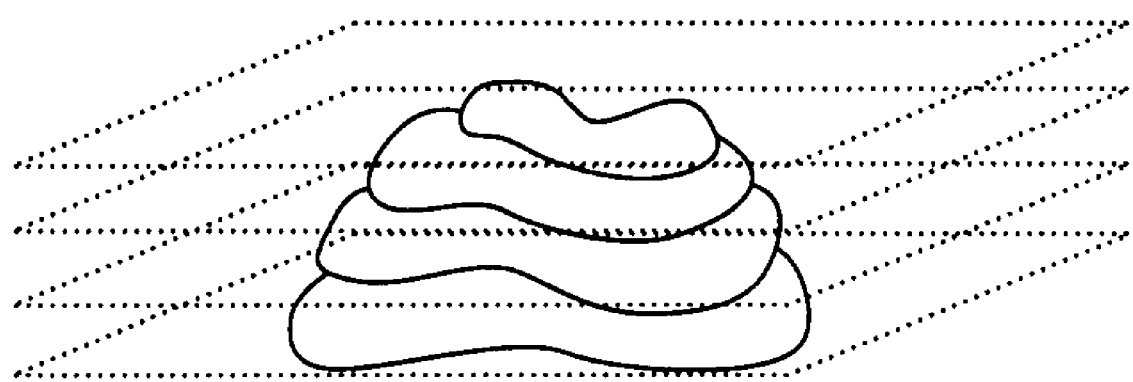
FIG. 1A illustrates a volume of interest defined by a stack of planar closed polygons.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, that may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient.

Some portions of the description that follow are presented in terms of algorithms and symbolic representations of operations on data bits that may be stored within a memory and operated on by a processor. These algorithmic descriptions and representations are the means used by those skilled in the art to effectively convey their work. An algorithm is generally conceived to be a self-consistent sequence of acts leading to a desired result. The acts are those requiring manipulation of quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, parameters, or the like.

It should also be noted that the methods and apparatus are discussed herein in relation to CT imaging only for ease of explanation. The method and apparatus discussed herein may also be used to generate VOIs from other types of medical diagnostic images (anatomical and/or functional), for example, magnetic resonance (MR), ultrasound (US), nuclear medicine (NM) PET/SPECT, etc. In addition, the "targets" discussed herein may be an anatomical feature(s) of a patient such as a pathological or normal anatomy and may include one or more non-anatomical reference structures.

Figure 2:
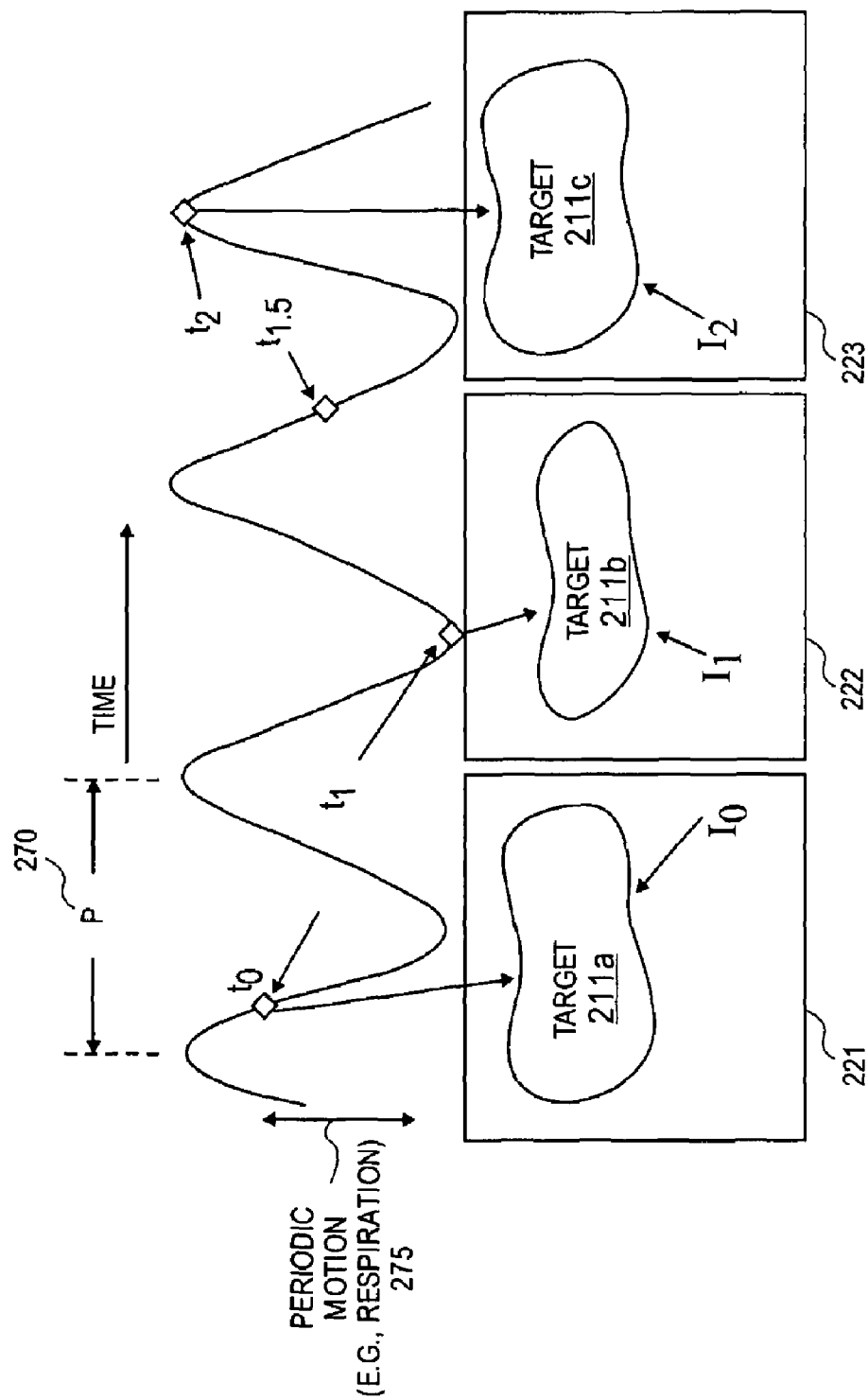
FIG. 2 illustrates one embodiment of the acquisition of pre-treatment images (e.g., CT scans) of a changing target within a patient's anatomy.

FIG. 2 illustrates one embodiment of the acquisition of pre-treatment images (e.g., CT scans) of a changing target within a patient's anatomy. In the illustrated embodiment, the target 211 (e.g., anatomical feature volume) may move or undergo a deformation (which may be a non-rigid deformation) during a patient's respiration, heartbeats, or other motion. While in embodiments herein the target 211 is described as moving periodically while undergoing a non-rigid deformation, any other type of motion (e.g. aperiodic motion) and any type of deformation or motion of the target may be accounted for. Furthermore, while embodiments may be discussed herein in regards to a CT scans, any other type of imaging modality may be used, for example, magnetic resonance imaging (MRI), positron emission tomography (PET), ultrasound, etc.

In one embodiment, CT scans (e.g., CT image 221, 222, 223) are taken at different times points $t_i$ within, for example, a breathing cycle P 270 of a patient. The time points $t_i$ correspond to different epochs in the patient breathing cycle, with, for example, $t_0<t_1<t_2$. The cycle P 270 may be monitored by an external sensor, for example, a breathing sensor, markers placed on the chest, etc. The CT images 221, 222, and 223 are taken at time points $t_0$, $t_1$, and $t_2$, respectively, containing the target 211a, 211b and 211c at those respective time points. The epochs or time points within the breathing cycle P 270 may be chosen to substantially encompass the overall dynamic range of the periodic motion 275. For example, in one embodiment, the time points may include: a time point $t_1$ corresponding to a trough of the cycle P; a time point $t_2$ corresponding to a peak of the cycle P; and a third time point $t_0$ disposed at an intermediate location between the peak and the trough of the cycle P 270. In other embodiments, the time points selected for taking the CT images may include fewer or more than the three time points $t_0$, $t_1$, and $t_2$ described above. Accordingly, fewer or more than three CT images may be used.

One way of providing a model for the continuous non-rigid deformation of the anatomy as a function of the motion cycle involves constructing a 4D mathematical model that morphs the CT image acquired at one instant or time point in the motion cycle into another CT image acquired at a subsequent instant or time point in the motion cycle. Any standard software and/or algorithm that is known and may be commercially available can be used to morph one image into another image, and to describe this in terms of a mathematical model. The 4D mathematical model relates the 3D locations of one or more reference structures (e.g., fiducals, skeletal structure, etc.) with the 3D locations of the target, as a function of the instant in the motion cycle. As such, if the deformation of the target is desired to be known at an intermediate position between CT images e.g., $t_{1.5}$, the 4D mathematical model is applied to every voxel in one of the acquired CT images (e.g., CT image 222) to map the deformation of the target in each voxel of the CT image. However, such a 4D mathematical modeling may require a lot of computing power and may be slower than desirable due the deformation mapping of each voxel in the CT image.

Described hereafter is a method and apparatus for tracking of a changing (e.g., moving, deforming, etc.) target 211 using a four-dimensional (4D) VOI, where the fourth dimension in the VOI architecture is a time dimension. A 4D VOI may be represented as a set $\{V_0, V_1, \ldots, V_k\}$ where each $V_i$ is a 3D VOI representing a given point in time. In one embodiment, such a 4D VOI may be created by generating a 3D VOI ($V_0$) in a 3D image $I_0$. In the above example, the first and second dimensions of the VOI correspond to one image slice in the 3D VOI and the third dimension corresponds to other slices in the 3D VOI. It should also be noted that the definitions of the first three dimensions could be the three axes of any coordinate system defined within the 3D image space.

Then, given subsequent images $\{I_0, I_1, \ldots, I_k\}$ taken at different times (e.g., to model anatomical change due to a patient's respiratory cycle), the corresponding VOIs could be formed by performing a non-rigid registration to determine the deformation mapping of image $I_0$ to image $I_i$, and applying the deformation mapping to $V_0$ to give an initial estimate of $V_i$. In one embodiment, one or more additional refinement steps may be applied to $V_i$, for example, a model-based refinement if $V_i$ represents an anatomical organ.

Figure 1B:
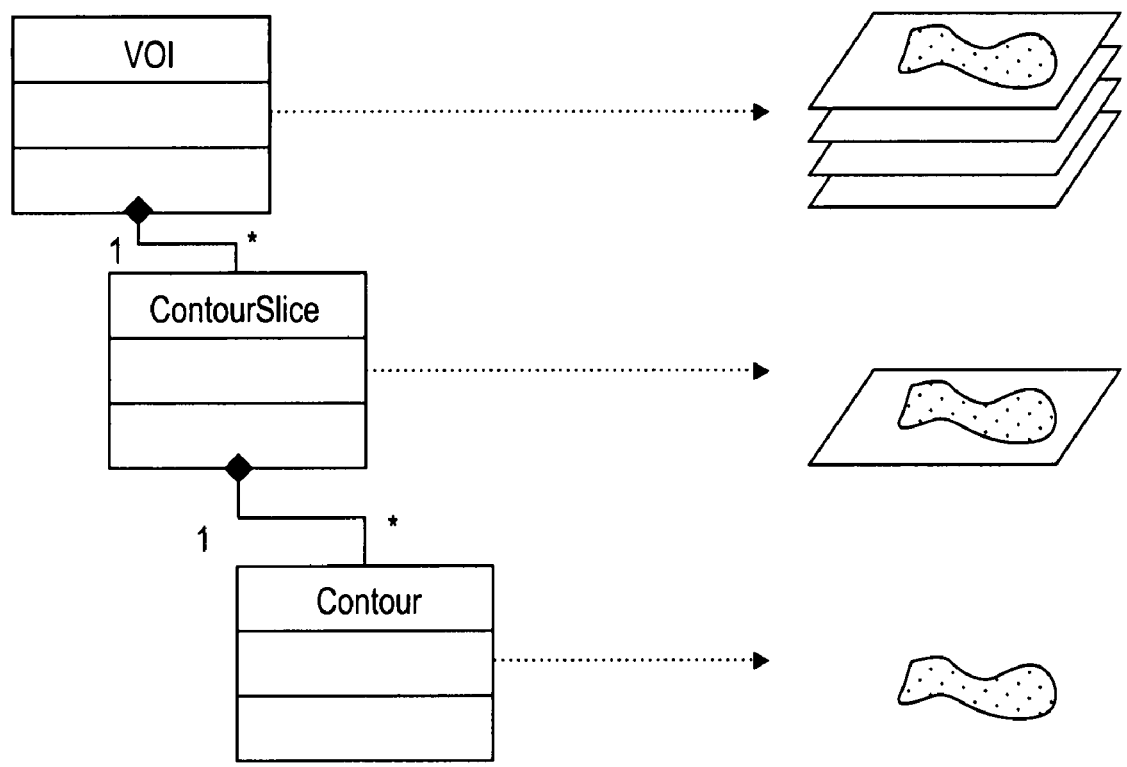
FIG. 1B illustrates a conventional three-tier VOI structure in a Unified Modeling Language (UML) graph with a sample VOI.

A VOI representing any given point in time may be formed by direct interpolation between $V_i$ and $V_{i+1}$, where i and i+1 are the VOIs immediately preceding and succeeding a desired point in time. This method may be much faster than having to interpolate the underlying deformation field itself and may result in a more efficient way of modeling tissue (e.g., organ) deformation over time. This is because the underlying deformation field maps the space of image $I_i$ to the space of image $I_{i+1}$, hence if the deformation field is used directly to map between $V_i$ and $V_{i+1}$ the underlying bit mask representation must be used (for example as described below in relation to FIG. 6). However, if interpolation is used between the contours (e.g., of FIG. 1A and FIG. 1B) of $V_i$ and $V_{i+1}$, it is possible to perform the interpolation much faster. In other words, instead of having to look up values of the deformation field for all the voxels within $V_i$ and $V_{i+1}$, the points on the contours of $V_i$ and $V_{i+1}$ may be directly interpolated to create a set of bounding contours for the intermediate VOI.

In one embodiment, the 4D VOI architecture may be used with a robotic based linear accelerator (LINAC) radiosurgery system (as discussed in further detail below) to supplement or supplant the robot motion tracking mechanisms that may already be present in such a system. Because the coordinate system in which each member of the VOI set is represented is arbitrary, a coordinate system may be chosen that is invariant with respect to the robotic-based LINAC. That is, the compensation for target change that would have otherwise been determined by the treatment delivery system for the robotic controlled LINAC during the treatment delivery is already predetermined by the treatment planning system using the 4D VOI architecture.

Figure 3:
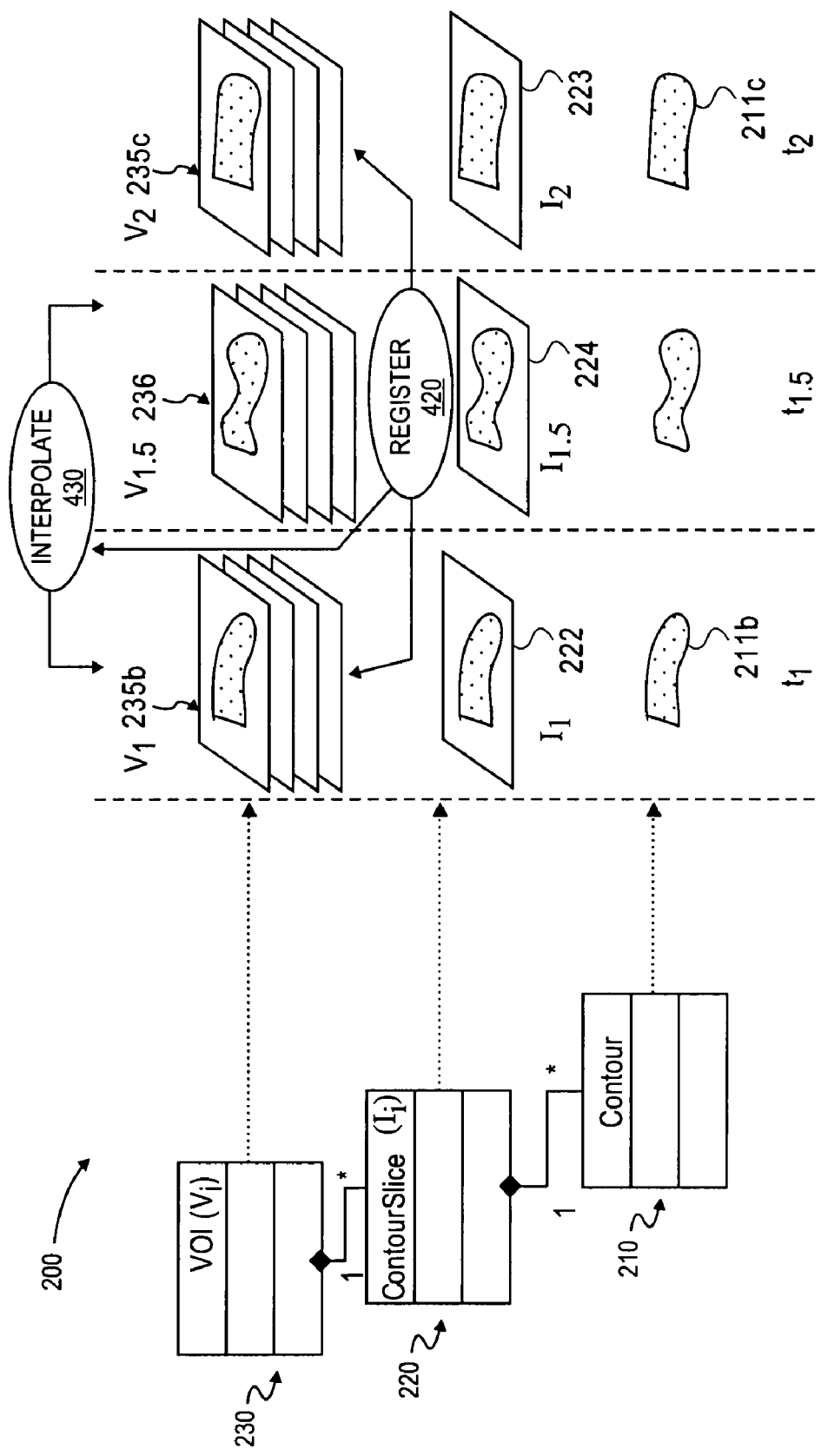
FIG. 3 illustrates one embodiment of a 4D VOI architecture, where the fourth dimension in the VOI architecture is a time dimension.

FIG. 3 illustrates one embodiment of a 4D VOI architecture, where the fourth dimension in the VOI architecture is a time dimension. In this embodiment, the VOI is represented using a three-tier structure (VOI-contourslice-contour) in a UML graph with an example target. UML is a graphical language for visualizing, specifying, constructing and documenting artifacts of a software-intensive system. The UML offers a standard way to write programming language statements, database schemas, and software components. UML is well known in the art; accordingly, a more detailed discussion is not provided herein. In one embodiment, each contour slice in VOI architecture 200 may be restricted so that it contains only a simple (i.e. closed boundary with no holes or intersections) contour. If this restriction is present, contour slices may be created in non-adjacent slices, and interpolation used to create the contours in the intermediate slices. In another embodiment, VOI architecture 200 allows multiple contours to be defined for each contour slice. In this case, VOIs with cavities, branches, and unconnected bodies may be drawn. Alternatively, the methods described herein may also be used with other tiered (e.g., 4 tier) VOI architectures.

In this embodiment, VOI architecture 200 includes a contour tier 210, a contour slice ($I_i$) tier 220, a VOI ($V_i$) tier 230. In this embodiment, the 4D VOI architecture 200 may represented as a set $\{V_0, V_1, \ldots, V_k\}$ where each of the $V_i$ is a 3D VOI representing a given point in time. Only three $V_i$ ($V_0$ 235a, $V_{1.5}$ 235b, and $V_2$ 235c) are illustrated for ease of discussion purposes. Continuing the example of FIG. 2, the CT slices 221 and 223 are taken at time points $t_1$ and $t_2$, respectively, containing the target 211 in its state (e.g., position and deformation) at those respective time points 211b and 211c.

Figure 4:
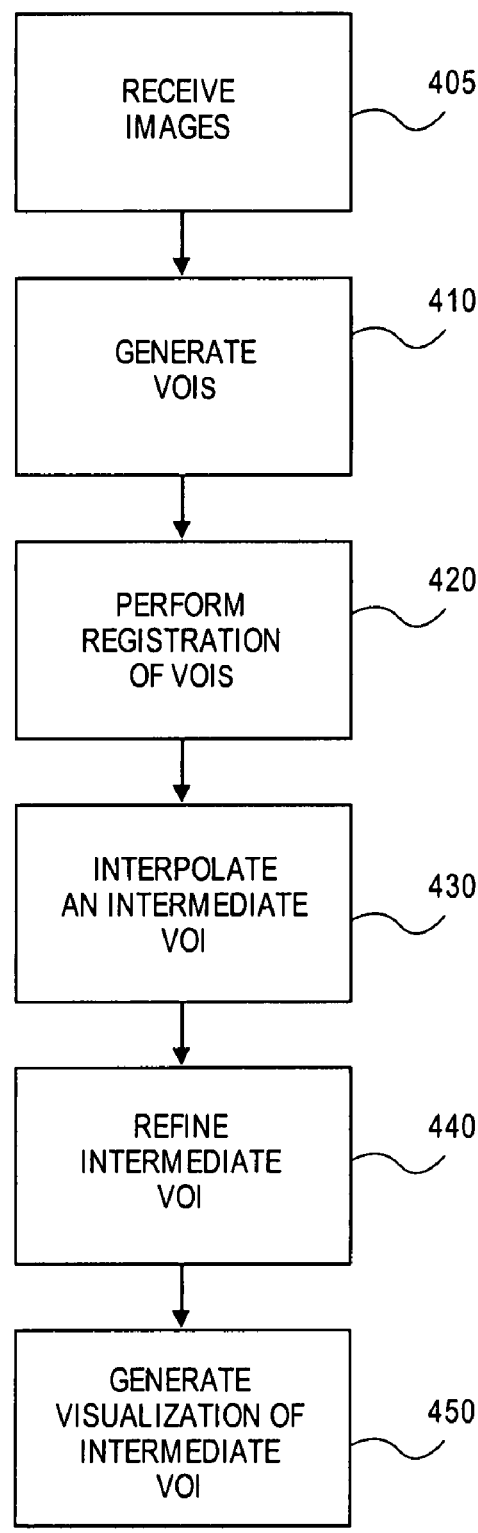
FIG. 4 illustrates one embodiment of generating a VOI using a 4D VOI architecture.

FIG. 4 illustrates one embodiment of generating a VOI using a 4D VOI architecture. In this embodiment, the method may include receiving at least two 3D images $I_1$ 222 and $I_2$ 223, step 405, and generating at least two 3D VOIs (e.g., $V_1$ and $V_2$) with the at least two corresponding 3D images $I_1$ 222 and $I_2$ 223, step 410. In step 420, a non-rigid registration of $V_1$ 235b and $V_2$ 235c is performed. Registration may be performed using techniques known to those of ordinary skill in the art; accordingly, a detailed description of registration is not provided. In one embodiment, for example, a registration technique as described in "Hybrid point-and-intensity based deformable registration for abdominal CT images", J. B. West, C. R. Maurer, Jr., and J. R. Dooley, Proc. SPIE vol. 5747, pp. 204-211, 2005, may be used. The output of the registration of step 420 may be referred to as a deformation field. A deformation field relating two images, A and B, is a set of vectors defined such that in any position x in image A, the corresponding element of the deformation field, D(x), is a vector v such that the position (x+v) in image B describes the same anatomical location as x in image A.

Then, in order to determine $V_{1.5}$ 236 at a time in between $t_1$ and $t_2$, an interpolation may be performed, using the registration results of step 420, on $V_1$ 235b and $V_2$ 235c, step 430. More generally, a VOI representing any given point in time may be formed by direct interpolation between $V_i$ and $V_{i+1}$, where i and i+1 are the 3D VOIs immediately preceding and succeeding a desired point in time. For example, a three-dimensional space deformation model, as described in "D. Bechmann and N. Dubreuil. Animation through space and time based on a space deformation model. The Journal of Visualization and Computer Animation. 4(3)165-184, 1993" may be used to generate the interpolated VOI.

In one embodiment, one or more additional refinements, step 440, may be applied to $V_{1.5}$ 236 such as a model-based refinement. With a model-based refinement, a model of $V_{1.5}$ 236 is used to ensure that the contours describing $V_{1.5}$ 236 give a valid shape for the organ being described by $V_{1.5}$ 236. In one embodiment of a model-based refinement, the principal modes of variation of the boundary of $V_{1.5}$ 236 are stored as part of the model, and the contours of $V_{1.5}$ 236 are refined so that their principal modes of variation are within given limits of those of the model. Refinement of a VOI may be performed either manually by the user (e.g., through a graphical user interface) or through the use of an algorithm that operates on the VOI.

Once $V_{1.5}$ 236 has been generated, it may be used to generate a visualization of the VOI at time point $t_{1.5}$, step 450. The generation of a visualization from a VOI could be achieved by rendering the mask volume of that VOI using volume rendering techniques as described in "Levoy, M., et. al, Volume Rendering in Radiation Treatment Planning, Proc. First Conference on Visualization in Biomedical Computing, IEEE Computer Society Press, Atlanta, Ga., May, 1990, pp. 4-10," or by directly rendering the 3D geometrical structure of that VOI. Using 4D VOI architecture 200, the visualization (e.g., images 222, 224 and 223) may be graphically displayed to a user to animate changing structures (e.g., image 211) faster and more accurate than may be possible when performing 4D mathematical modeling to map the underlying deformation field itself.

Figure 5:
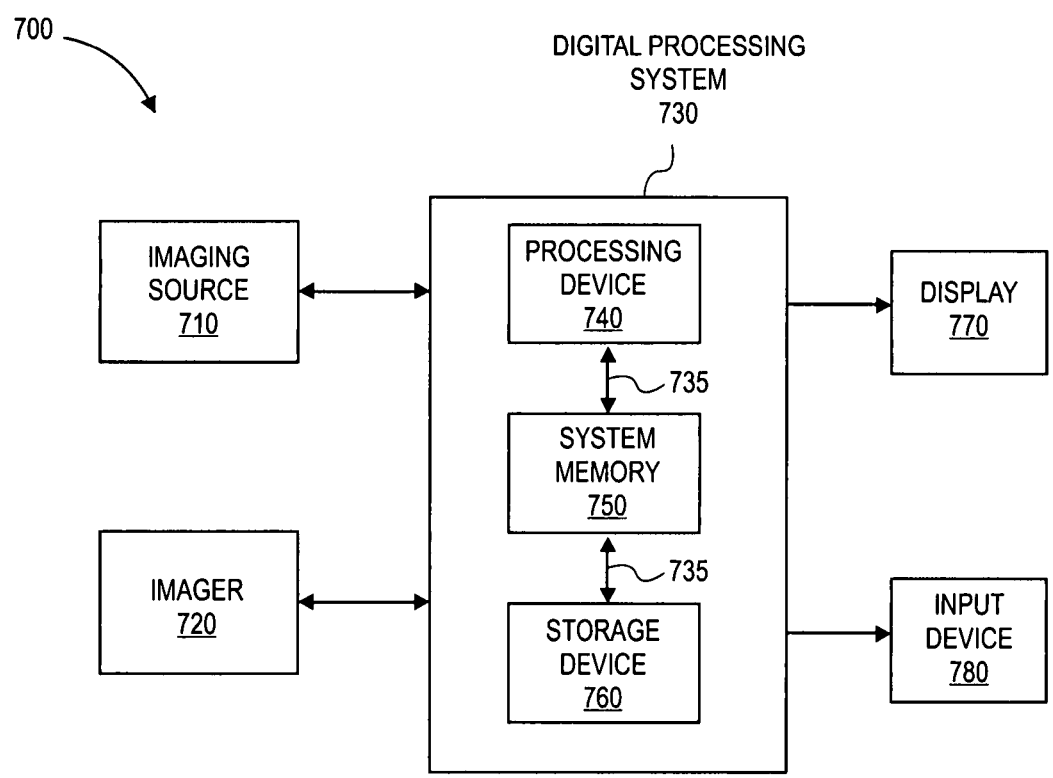
FIG. 5 illustrates of medical diagnostic imaging system implementing one embodiment of the present invention.

FIG. 5 illustrates one embodiment of medical diagnostic imaging system in which features of the present invention may be implemented. The medical diagnostic imaging system may be discussed below at times in relation to CT imaging modality only for ease of explanation. However, other imaging modalities may be used as previously mentioned.

Medical diagnostic imaging system 700 includes an imaging source 710 to generate a beam (e.g., kilo voltage x-rays, mega voltage x-rays, ultrasound, MRI, etc.) and an imager 720 to detect and receive the beam generated by imaging source 710. In an alternative embodiment, system 700 may include two diagnostic X-ray sources and/or two corresponding image detectors. For example, two x-ray sources may be nominally mounted angularly apart (e.g., 90 degrees apart or 45 degree orthogonal angles) and aimed through the patient toward the imager(s). A single large imager, or multiple imagers, can be used that would be illuminated by each x-ray imaging source. Alternatively, other numbers and configurations of imaging sources and imagers may be used.

The imaging source 710 and the imager 720 are coupled to a digital processing system 730 to control the imaging operation. Digital processing system 730 includes a bus or other means 735 for transferring data among components of digital processing system 730. Digital processing system 730 also includes a processing device 740. Processing device 740 may represent one or more general-purpose processors (e.g., a microprocessor), special purpose processor such as a digital signal processor (DSP) or other type of device such as a controller or field programmable gate array (FPGA). Processing device 740 may be configured to execute the instructions for performing the operations and steps discussed herein. In particular, processing device 740 may be configured to execute instructions to perform the Boolean operations on the contour sets 241-244 to define VOI 231 as discussed above with respect to FIG. 3 and to generate a VOI mask volume as discussed above with respect to FIG. 5.

Digital processing system 730 may also include system memory 750 that may include a random access memory (RAM), or other dynamic storage device, coupled to bus 735 for storing information and instructions to be executed by processing device 740. System memory 750 also may be used for storing temporary variables or other intermediate information during execution of instructions by processing device 740. System memory 750 may also include a read only memory (ROM) and/or other static storage device coupled to bus 735 for storing static information and instructions for processing device 740.

A storage device 760 represents one or more storage devices (e.g., a magnetic disk drive or optical disk drive) coupled to bus 735 for storing information and instructions. Storage device 760 may be used for storing instructions for performing the steps discussed herein.

Digital processing system 730 may also be coupled to a display device 770, such as a cathode ray tube (CRT) or liquid crystal display (LCD), for displaying information (e.g., image slice, animation of the target using the 4D VOI, etc.) to the user. An input device 780, such as a keyboard, may be coupled to digital processing system 730 for communicating information and/or command selections to processing device 740. One or more other user input devices, such as a mouse, a trackball, or cursor direction keys for communicating direction information and command selections to processing device 740 and for controlling cursor movement on display 770 may also be used.

It will be appreciated that the digital processing system 730 represents only one example of a system, which may have many different configurations and architectures, and which may be employed with the present invention. For example, some systems often have multiple buses, such as a peripheral bus, a dedicated cache bus, etc.

One or more of the components of digital processing system 730 may form a treatment planning system. The treatment planning system may share its database (e.g., stored in storage device 760) with a treatment delivery system, so that it is not necessary to export from the treatment planning system prior to treatment delivery. The treatment planning system may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view isodose distributions on any one of various imaging modalities (e.g., MRI, CT, PET, etc.).

In one embodiment, the treatment delivery system may be an image guided robotic based linear accelerator (LINAC) radiation treatment (e.g., for performing radiosurgery) system, such as the CyberKnife® system developed by Accuray, Inc. of California. In such a system, the LINAC is mounted on the end of a robotic arm having multiple (e.g., 5 or more) degrees of freedom in order to position the LINAC to irradiate the pathological anatomy with beams delivered from many angles in an operating volume (e.g., sphere) around the patient. Treatment may involve beam paths with a single isocenter, multiple isocenters, or with a non-isocentric approach (i.e., the beams need only intersect with the pathological target volume and do not necessarily converge on a single point, or isocenter, within the target). Treatment can be delivered in either a single session (monofraction) or in a small number of sessions (hypo-fractionation) as determined during treatment planning. Treatment may also be delivered without the use of a rigid external frame for performing registration of pre-operative position of the target during treatment planning to the intra-operative delivery of the radiation beams to the target according to the treatment plan.

Alternatively, another type of treatment delivery systems may be used, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time for which the subset of beams should be exposed, so that the dose constraints are best met.

In other embodiments, yet other types of treatment delivery systems may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

The 4D VOI architecture described herein may be used to perform inverse planning. Inverse planning, in contrast to forward planning, allows the medical physicist to independently specify the minimum tumor dose and the maximum dose to other healthy tissues, and lets the treatment planning software select the direction, distance, and total number and energy of the beams. Conventional treatment planning software packages are designed to import 3-D images from a diagnostic imaging source, for example, magnetic resonance imaging (MRI), positron emission tomography (PET) scans, angiograms and computerized x-ray tomography (CT) scans. These anatomical imaging modalities such as CT are able to provide an accurate three-dimensional model of a volume of interest (e.g., skull or other tumor bearing portion of the body) generated from a collection of CT slices and, thereby, the volume requiring treatment can be visualized in three dimensions.

During inverse planning, the VOI 230 is used to delineate structures to be targeted or avoided with respect to the administered radiation dose. That is, the radiation source is positioned in a sequence calculated to localize the radiation dose into VOI 230 that as closely as possible conforms to the target (e.g., pathological anatomy such as a tumor) requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of radiation treatment system, to meet the min/max dose constraints of the treatment plan.

The 4D VOI architecture 200 may be used to create a 4D mask volume, as discussed in further detail below. Hence, beams may be enabled or disabled depending the target's change over time. Although the change in target during treatment delivery may be different than the change in the target during treatment planning (e.g., due to differences in a patient's respiration at those different times), certain gross changes may be assumed to be similar. Accordingly, in one embodiment, the 4D VOI architecture 200 may be used to supplement (or possibly supplant) the robot motion tracking mechanisms that may otherwise be present in a robotic-based LINAC radiation treatment system, with finer changes handled by dynamic tracking capabilities of the treatment delivery system. Dynamic tracking is known in the art; accordingly a detailed description is not provided. Alternatively, the 4D VOI architecture 200 may be used to supplant the robot motion tracking mechanisms that may otherwise be present in a robotic-based LINAC radiation treatment system.

Because the coordinate system in which each member of the set is represented is arbitrary, a coordinate system that is invariant with respect to the robot. That is, the compensation for target motion is already taking into account by the treatment planning software using the 4D VOI architecture 200.

Figure 6:
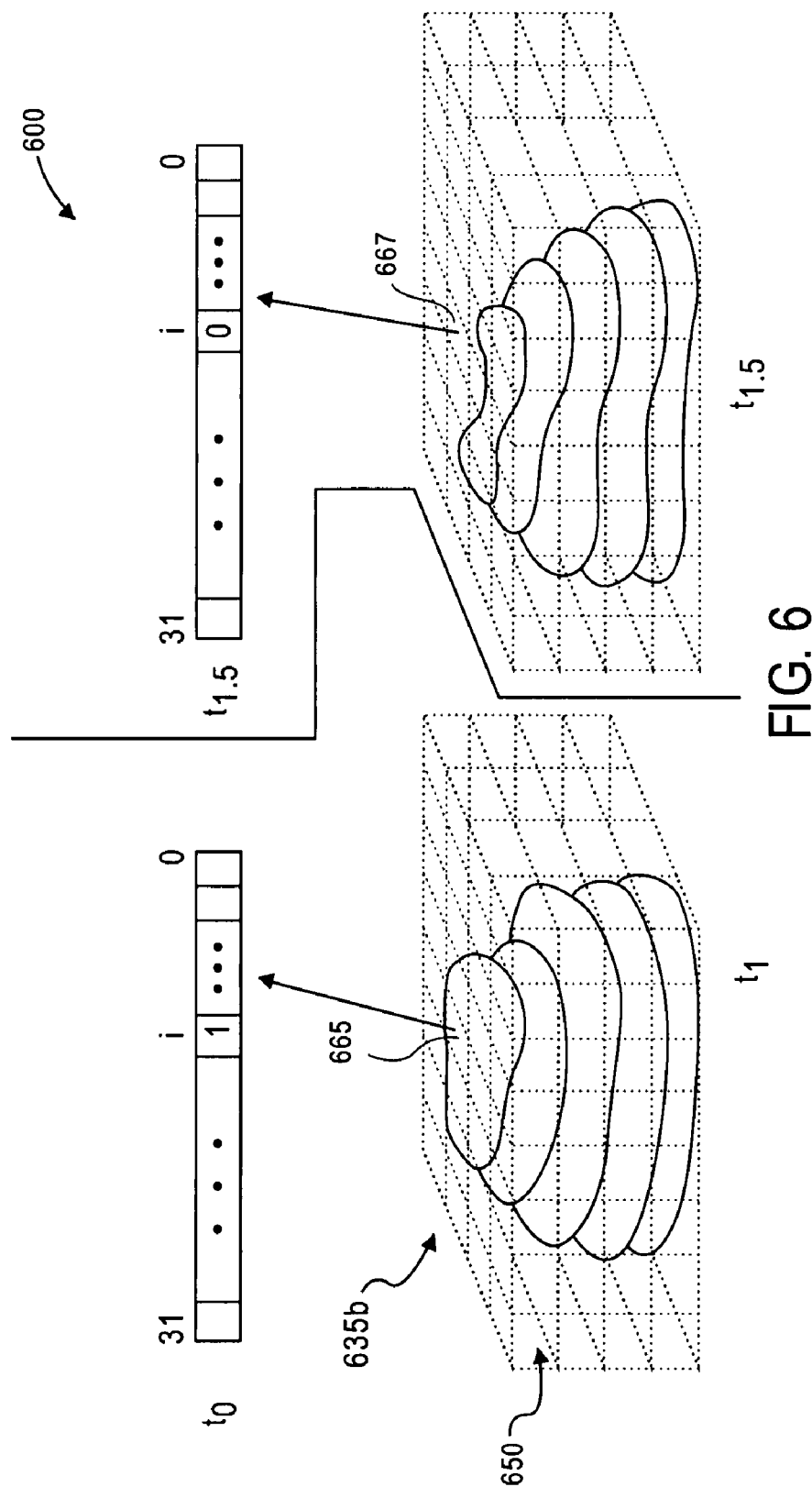
FIG. 6 illustrates one embodiment of a 4D mask volume.

FIG. 6 illustrates one embodiment of a 4D mask volume. For ease of discussion, 4D mask volume 600 is shown with two overlaid masks 635$b$ and 636 on $V_1$ 235$b$ and $V_{1.5}$ 236, respectively, for times $t_i$ and $t_{1.5}$, respectively. The VOI mask volumes 635$b$ and 636 are volume representations of all user defined VOIs that are geometrically considered as a cuboid composed of many small cuboids of the same size (i.e., the voxels). In this embodiment, every voxel (e.g., voxels 650, 665, etc.) contains 32 bits. Alternatively, other number of bit words may be used for a voxel. One bit, or more, of a voxel (e.g., the $i_{th}$ bit) may be used to represent if the voxel is covered by a VOI that is defined by the index of the bit. At every voxel location (e.g., voxel 665), the bit value will be either a "1" or a "0" indicating whether a particular voxel is part of the target. For example, a "1" bit value may be used to indicate a voxel is contained within the VOI represented by that mask position (as conceptually illustrated by the "1" for $i_{th}$ bit of voxel 665 of mask 635$b$). If, for example, the voxel bit is a "0" (as conceptually illustrated by the "0" for the ith bit of voxel 667 of mask 636), the treatment planning algorithm ignores the dose constraints for that corresponding voxel. The VOI mask volume serves as an interface between the VOI structures and the rest of an imaging system's functions such as, for examples, a 4-D VOI visualization and dose calculation in treatment planning. Using the 4D mask volume 600, the radiation beams of a treatment delivery system may be enabled or disabled based on a target's change in position.

The dose calculation process in the treatment planning algorithm considers a set of beams that are directed at the target region 211. In one embodiment, the treatment planning algorithm is used with a radiation source that has a collimator that defines the width of the set of beams that is produced. For each target 211, for example, the number of beams, their sizes (e.g., as established by the collimator), their positions and orientations are determined. Having defined the position, orientation, and size of the beams to be used for planning, how much radiation should be delivered via each beam is also determined. The total amount of radiation exiting the collimator for one beam is defined in terms of Monitor Units (MU). Because the intensity of the radiation source is constant, the MU is linearly related to the amount of time for which the beam is enabled. The radiation dose absorbed (in units of cGy) by tissue in the path of the beam is also linearly related to the MU. The absorbed dose related to a beam is also affected by the collimator size of the beam, the amount of material between the collimator and the calculation point, the distance of the collimator from the calculation point, and the distance of the calculation point from the central axis of the beam.

Figure 7:
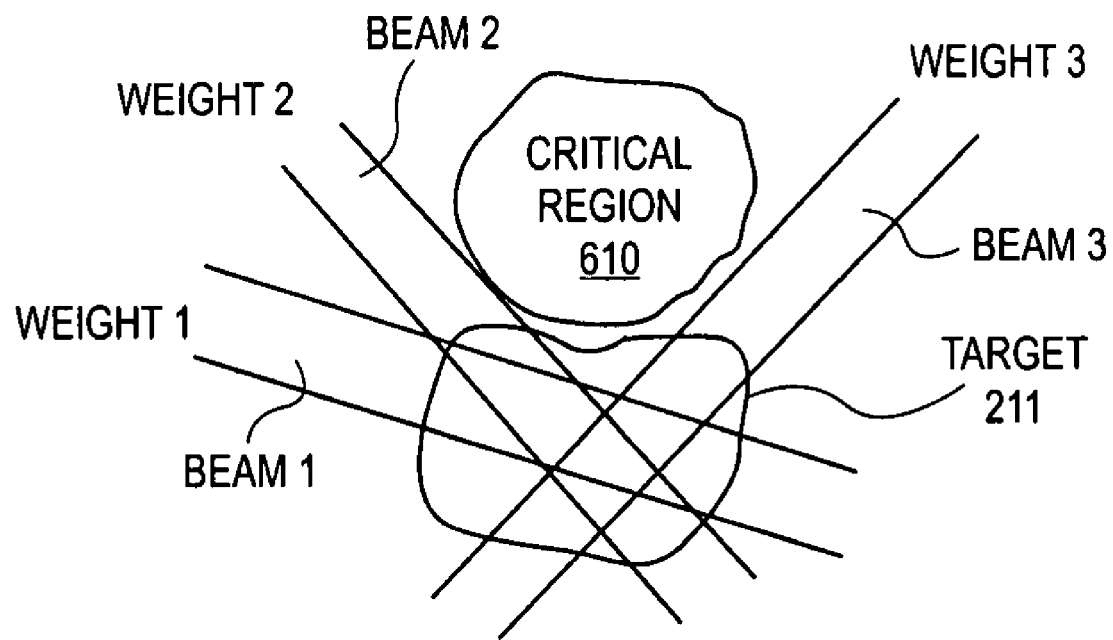
FIG. 7 illustrates a 2-dimensional perspective of radiation beams of a radiation treatment system directed at a target region according to a treatment plan.

FIG. 7 illustrates a 2-dimensional perspective of radiation beams of a radiation treatment system directed at a target region according to a treatment plan. It should be noted that 3 beams are illustrated in FIG. 7 only for ease of discussion and that an actual treatment plan may include more, or fewer, than 3 beams. Furthermore, although the 3 beams appear to intersect in the 2-dimensional perspective of FIG. 7, the beams may not intersect in their actual 3-dimensional space. The radiation beams need only intersect with the target volume and do not necessarily converge on a single point, or isocenter, within the target. In one embodiment, using 4D mask volume 600 beams may be enabled or disabled based on the change in the target over time.

Figure 8:
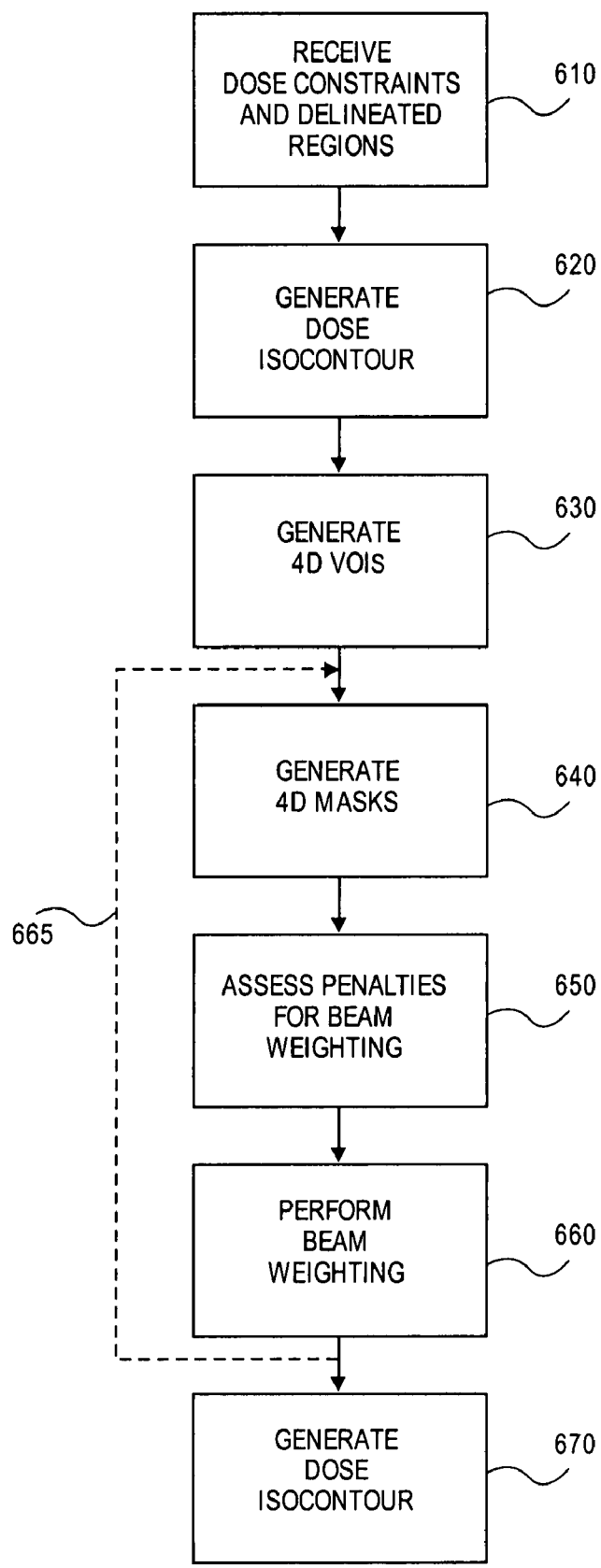
FIG. 8 is a flow chart illustrating one embodiment of generating a treatment plan using a 4D mask volume.

FIG. 8 is a flow chart illustrating one embodiment of generating a treatment plan using a 4D mask volume. In one embodiment, the treatment planning algorithm receives as input from a user, step 610, the delineated target region 220 and any critical region 210 on one or more slices of a CT image; and (2) dose constraints defining the minimum and maximum doses for target region 220 and the maximum dose for the critical region 210. It should be noted that additional dose constraints for additional regions may also be provided. The delineation of the regions and the dose constraints may be performed in any order.

Then, the treatment planning algorithm performs beam weighting of each one or more beams of the radiation treatment system to be used in the treatment plan according to the inputs provided by the user above. The user or the treatment planning algorithm assigns an arbitrary weighting to each of one or more beams (e.g., beam 1, beam 2, beam 3 of FIG. 7) of the radiation treatment system. This weighting may be determined using an algorithm designed to give a suitable "start point" for planning, may be randomly chosen, or may simply be a constant weighting for each beam.

In step 630, the 4D VOI is generated and, in step 640, the 4D mask volume is generated with the methods discussed above in relation to FIGS. 3 and 4. If a voxel bit from a 4D volume mask 600 is a "0", the planning algorithm ignores the dose constraints for that corresponding dose voxel for the particular point in time VOI. However, if a voxel bit from dose contour mask 400 has a "1" bit value for a particular point in time VOI, then determine whether any penalties should be accessed when performing beam weighting based on the dose constraints for that dose voxel, step 650. In one embodiment, in order to reduce dose to a given sensitive organ to minimal levels, the 4D volume mask may be used so that if the 3D VOI at any of the time points has a "1" bit value at any position intersected by a beam, that beam is automatically set to have zero MU in the final plan.

In one embodiment, the following algorithm may be used to perform beam weighting. In this embodiment, to begin the beam weighting, step 660, an assumption may be made that the size and trajectory of the beam set has been defined. Let the beam set be $\{B_i; 1 \leq i \leq N\}$, where $N \approx 500$. Beam 1, beam 2, and beam 3 illustrate in FIG. 7 have a respective weight 1, weight 2, weight 3 (i.e., a number of MU assigned to the beam, or how long a beam will be maintained on) associated with it. The weight in MU of each beam is designated by $w_i$. The delineated regions are represented as objects $T_j$ (derived from the 4D mask volume 600), with corresponding minimum and maximum allowed dose $min_j$ and $max_j$, and critical structures (critical region 210) $C_j$, with corresponding $max_j$ defined. Each region has an integer priority $p_j \in [0,100]$ defining the relative importance of the dose constraints applied to that region. For each beam, a 4D dose value mask is created. The 4D dose value mask may be regarded as a set of 3D dose value masks, in the same way that a 4D VOI is a set of 3D VOIs. Each 3D dose value mask provides a linked list of floating point values and positions $d_i(r,t)$ at a given point in time, where r is the position within the dose calculation volume, and di is the dose in cGy delivered to r by beam i when $w_i$ is set to unity, and t is the time, represented as a position in the respiratory cycle. Thus, the total dose at r, at position t in the respiratory cycle is given by:

$$D(r, t) = \sum_{i=1}^{N} w_i d_i(r, t).$$

Hence the total dose at r, summed over the entire respiratory cycle is, $$D(r) = \sum_{t} D(r, t), \quad (1)$$

and the total dose for beam i, summed over the entire respiratory cycle is, $$d_i(r) = \sum_{t} d_i(r, t)$$

For each $B_i$, we define a beam value $v_i$, where $$v_i = \frac{\sum_{j} \sum_{r \in T_j} d_i(r)}{\sum d_i(r)}, \quad (2)$$

The beam value is the ratio of dose delivered into target region 220 to total dose delivered. To define the initial set of $w_i$ for optimization, we set $w_i = v_i$, $\forall i$. The maximum dose within the dose calculation volume, $D_{max}$, is computed and the beam weights renormalized so that the new maximum dose is equal to the largest of the maximum dose constraints, $max_j$. Hence, this provides:

$$w_i = v_i sup(max_j)/D_{max}. \quad (3)$$

At one iteration of the treatment planning algorithm, the optimization process looks at all of the dose values in the dose volume and determine if the target region 211 and a critical region 610 are within the dose constraints. For example, suppose the dose in the target region 211 is specified to be equal to or greater than 2000 cGy and less than or equal to 2500 cGy. Suppose, the current dose value at grid location for voxel 665 of FIG. 6 is 1800 cGy, then the optimization process determines that, at the current beam weightings, the dose value at voxel 665 is 200 cGy short in order to satisfy the treatment plan constraints.

Given the initial weights, the optimization process then alters the beam weights so that the treatment solution is closer to meeting the provided dose constraints. First, a set of $\Delta w_i$, the amount by which each beam weight may be changed, is defined:

$$\Delta w_i = \Delta^{(0)} w_i = \frac{s}{4N} \sum_{i=1}^{N} w_i, \forall i \quad (4)$$

where s is the search resolution, having an initial value of 1.

The optimization process iterates through one or more of the beams and for each of the beams, if a beam weight is increased or decreased by a certain amount, determines the resulting dose distribution from such a change (i.e., how such a change alters the amount of violation of the treatment plan constraints). For example, an increase in one or more of the beam weights may typically help in achieving the constraint in the target (e.g., tumor) region but, depending on the location of the beam, it may also hurt in the critical region due to a possible resulting increase of dose above the maximum value in the critical region.

The optimization process traverses the volume of interest, adds up all the penalties that are incurred by the increase in a beam weight, adds up all the penalties that are incurred by the decreasing the beam weight (e.g., under-dosing the target region), and then provides a result. In one embodiment, a multiplier may be used with each penalty to stress the importance of one constraint (e.g., minimum dose value in the target region) versus another constraint (e.g., maximum dose value in the target region). For example, it may more important to achieve a minimum dose value than to stay under the maximum dose value in the target region.

The optimization process then updates the dose and goes on to the next beam and repeats the process until it has made its way through the beam set. The optimization process then reaches a stage where it has looked at all of the different weights for each of the beams at the different dose levels and selects the beam weight that provides the optimal resulting dose values in both the target region and critical region.

In one embodiment, an iterative optimization process is used as follows: Iterate over the beams in decreasing order of $v_i$. For each beam $B_j$, calculate $P_j^+$ and $P_j^-$, the relative penalties for respectively increasing or decreasing $w_j$, that are defined as:

$$P_j^+ = \sum_i \frac{p_i}{V_i} \sum_{r \in T_i \cup C_i} \Delta w_j d_j(r) \max\left(0, \min\left(1, \frac{D(r) + \Delta w_j d_j(r) - \max_i}{\Delta w_j d_j(r)}\right)\right) -$$

$$\sum_i \frac{p_i}{V_i} \sum_{r \in T_i} \Delta w_j d_j(r) \max\left(0, \min\left(1, \frac{\min_i - D(r)}{\Delta w_j d_j(r)}\right)\right),$$

and $$P_j^- = \sum_i \frac{p_i}{V_i} \sum_{r \in T_i} \Delta w_j d_j(r) \max\left(0, \min\left(\frac{\min_i - D(r) + \Delta w_j d_j(r)}{\Delta w_j d_j(r)}\right)\right) -$$

$$\sum_i \frac{p_i}{V_i} \sum_{r \in T_i \cup C_i} \Delta w_j d_j(r) \max\left(0, \min\left(1, \frac{D(r) - \max_i}{\Delta w_j d_j(r)}\right)\right),$$

where $V_i$ is the volume in mm$^3$ of region i. Hence, the penalty for this beam is the sum of the additional amount of over-dosing and under-dosing that would be created by the change in the beam, weighted by the priorities of the different regions and normalized according to the region volumes. If $P_j^-$ and $P_j^+$ are both positive, $w_j$ is kept the same, otherwise change $w_j = w_j \pm \Delta w_j$ according to whichever of $P_j^-$ and $P_j^+$ is smaller. If the previous iteration moved $w_j$ in the same direction as this iteration, the following is set:

$$\Delta w_j = \Delta w_j + \Delta^{(0)} w_j, \quad (5)$$

i else set:

$$\Delta w_j = \Delta^{(0)} w_j. \quad (6)$$

The change in dose according to $\Delta w_j$ is computed and applied to the dose volume before the optimization process moves on to a next beam, because a correct decision on how to change the beam weight assumes an up-to-date view of the dose including change sin previous $w_i$. If all $w_j$ remained unchanged by the current iteration, s is reduced by a factor of 2.

In an alternative embodiment, the optimization algorithm may perform convex optimization via, for example, the Simplex algorithm, in an attempt to find an MU setting for all beams so that the dose constraints are nowhere violated. The Simplex algorithm is known in the art; accordingly, a detailed description is not provided. Alternatively, other iterative and non-iterative optimization algorithms may be used.

The 4D VOI architecture 200 may also be used with a mixed planning in which part of the treatment dose is generated by an isocenter placed using forward planning and part generated by individual beams during inverse planning.

It should be noted that although discussed at times herein in regards to radiation treatment, the methods and apparatus described herein are not limited for use solely in treatment planning but may also be used independently for other applications, such as simulation and animation of object changes (e.g., deformation) over time. In alternative embodiments, the methods and apparatus herein may be used outside of the medical technology field, such as non-destructive testing of materials (e.g., motor blocks in the automotive industry and drill cores in the petroleum industry) and seismic surveying.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   interpolating between 3D models of a volume of interest (VOI) generated from 3D anatomical images captured at different points in time, wherein the VOI includes a moving 3D anatomical target;
   modeling motion and deformation of the 3D anatomical target; and
   planning trajectories of a radiation treatment beam before treatment to deliver radiation treatment to the moving 3D anatomical target during treatment.

2. The method of claim 1, wherein interpolating between 3D models of the VOI comprises:
   generating a first VOI including the target at a first point in time;
   generating a second VOI including the target at a second point in time;
   registering the first VOI with the second VOI; and
   interpolating a third VOI including the target at a third point in time based on the registering of the first VOI with the second VOI. the third point in time being between the first and second points in time.

3. The method of claim 2, further comprising generating a visualization of the third VOI.

4. The method of claim 3, wherein generating the visualization comprises rendering a mask volume of the third VOI.

5. The method of claim 4, wherein rendering comprises volume rendering.

6. The method of claim 4, wherein rendering comprises direct rendering of a three-dimensional geometrical structure of the third VOI.

7. The method of claim 3, further comprising refining the third VOI.

8. The method of claim 7, wherein refining comprises a model-based refinement.

9. The method of claim 8, wherein the third VOI is changed with respect to at least one of the first and second VOIs.

10. The method of claim 2, further comprising:
    receiving a first image having the target at the first point in time; and
    receiving a second image having the target at the second point in time.

11. The method of claim 2, wherein the target at the first time point is changed with respect to the target at the second time point based on motion adjacent the target.

12. The method of claim 11, wherein the motion comprises a periodic motion characterized by a cycle.

13. The method of claim 1, wherein the 3D anatomical images comprise computed tomography images.

14. An article of manufacture, comprising a machine-accessible medium including data that, when accessed by a machine, cause the machine to perform operations comprising:
   interpolating between 3D models of a volume of interest (VOI) generated from 3D anatomical images captured at different points in time, wherein the VOI includes a moving 3D anatomical target;
   modeling motion and deformation of the 3D anatomical target; and
   planning trajectories of a radiation treatment beam before treatment to deliver radiation treatment to the moving 3D anatomical target during treatment.

15. The article of manufacture of claim 14, wherein interpolating between 3D models of the VOI comprises:
   generating a first VOI including a target at a first point in time;
   generating a second VOI including the target at a second point in time;
   registering the first VOI with the second VOI; and
   interpolating a third VOI including the target at a third point in time based on the registering, the third point in time being between the first and second points in time.

16. The article of manufacture of claim 15, wherein the instructions further cause the processor to perform operations comprising generating a visualization of the third VOI.

17. The article of manufacture of claim 16, wherein the instructions further cause the processor to perform operations comprising refining the third VOI.

18. The article of manufacture of claim 16, wherein generating the visualization comprises rendering a mask volume of the third VOI.

19. An apparatus, comprising:
   a storage device to store 3D images of a volume of interest (VOI) captured at different points in time, wherein the VOI includes a moving 3D anatomical target; and
   a processor coupled to the storage device, the processor configured to:
      generate 3D models of the VOI at the different points in time;
      interpolate between the 3D models to model motion and deformation of the 3D anatomical target; and
      generate a pre-treatment radiation treatment plan comprising radiation beam trajectories to deliver radiation to the moving 3D anatomical target during treatment.

20. The apparatus of claim 19, wherein the processor is:
   configured to receive first and second 3D images, the processor to generate a first VOI model including the target at a first point in time and a second VOI model including the target at a second point in time, the processor further to register the first VOI model with the second VOI model and interpolate a third VOI model including the target at a third point in time based on the registering, the third point in time being between the first and second points in time.

21. The apparatus of claim 20, wherein the processor is further configured to generate a visualization of the third VOI.

22. The apparatus of claim 21, wherein the processor is further configured to refine the third VOI.

23. The apparatus of claim 21, wherein the processor is further configured to render a mask volume of the third VOI.

24. The apparatus of claim 21, further comprising an imager coupled to the storage device, the imager to generate the first and second 3D images.

25. A method of tracking a changing target within an anatomical region to deliver radiation to the target during motion of the anatomical region, the method, comprising:
   determining, at a time of treatment planning. a plurality of locations of the target over time using a four-dimensional volume of interest (VOI) having a fourth dimension being a time dimension;
   determining, at a time of treatment planning using the four-dimensional VOI, one or more radiation beam trajectories to be delivered to the target within the moving anatomical region at a time of treatment delivery, wherein determining comprises performing at least one of enabling and disabling of the one or more radiation beams depending whether the one or more radiation beams intersect the target at the plurality of locations of the target determined using the four-dimensional VOI; and
   generating the four-dimensional VOI, wherein generating comprises:
      generating a first VOI including the target at a first point in time;
      generating a second VOI including the target at a second point in time;
      registering the first VOI with the second VOI; and
      interpolating a third VOI including the target at a third point in time based on the registering of the first VOI with the second VOI, the third point in time being between the first and second points in time.

26. The method of claim 25, wherein the target at the first time point is changed with respect to the target at the second time point based on the motion of the anatomical region.

27. The method of claim 26, wherein the motion comprises a periodic motion characterized by a cycle.

28. An apparatus. comprising:
   means for directly interpolating between a first contour of a first volume of interest (VOI) and a second contour of a second VOI using one or more points on the first and second contours; and
   means for generating an intermediate contour of an intermediate VOI based on the interpolating, wherein the means for directly interpolating comprises a four-dimensional VOI having a fourth dimension being a time dimension, and wherein the apparatus further comprises:
   means for determining, at a time of treatment planning, a plurality of locations of a target over time using the four-dimensional volume of interest (VOI); and
   means for determining, at a time of treatment planning using the four-dimensional VOI, one or more radiation beam trajectories to be delivered to the target within the moving anatomical region at a time of treatment delivery.

* * * * *